(12) United States Patent
Stauffer

(10) Patent No.: US 7,649,116 B1
(45) Date of Patent: Jan. 19, 2010

(54) FORMATION OF OLEFINS FROM METHYL MERCAPTAN

(76) Inventor: John E. Stauffer, 6 Pecksland Rd., Greenwich, CT (US) 06830

( * ) Notice: Subject to any disclaimer, the term of this patent is extended or adjusted under 35 U.S.C. 154(b) by 6 days.

(21) Appl. No.: 12/057,734

(22) Filed: Mar. 28, 2008

Related U.S. Application Data

(63) Continuation of application No. 11/443,885, filed on May 31, 2006, now Pat. No. 7,381,847.

(51) Int. Cl.
*C07C 319/00* (2006.01)
(52) U.S. Cl. ........................................................ 568/72
(58) Field of Classification Search .................. 568/72
See application file for complete search history.

(56) References Cited

U.S. PATENT DOCUMENTS 4,120,944 A * 10/1978 Kubicek ..................... 423/416
6,472,569 B1 10/2002 Wu

OTHER PUBLICATIONS

Boivin et al., {Pyrolysis of ethyl mercaptan, Canadian Journal of Chemistry (1955), 33, 1281-1285}.*
J.B. Conant and A.H. Blatt, Compounds Containing Sulfur, The Chemistry of Organic Compounds, 3rd ed., The MacMillan Co., New York, 1947 pp. 342-343.
Gerald Parkinson, ed., Chementator, Chemical Engineering, Jan. 1996, p. 17.
Kirk-Othmor, 4th ed. Thiols, John Wiley & Sons, p. 27.
Olah et al., {Onium Ylide chemistry. 1. Bifunctional acid-base-catalyzed conversion of heterosubstituted methanes into ethylene and derived hydrocarbons. The onium ylide mechanism of the C1 to C2 conversion, J. Am. Chem. Soc.; 1984; 106(7); 2143-2149}.

* cited by examiner

*Primary Examiner*—Daniel M Sullivan
*Assistant Examiner*—Chukwuma O Nwaonicha
(74) *Attorney, Agent, or Firm*—Young Basile

(57) ABSTRACT

A process is disclosed for the production of olefins including ethylene, propylene and butenes from methyl mercaptan. The process comprises a reaction whereby methyl mercaptan produces the olefin and hydrogen sulfide by pyrolysis. The reaction is carried out at an elevated temperature in the range of 300° C. to 600° C. to achieve the pyrolysis.

5 Claims, 1 Drawing Sheet

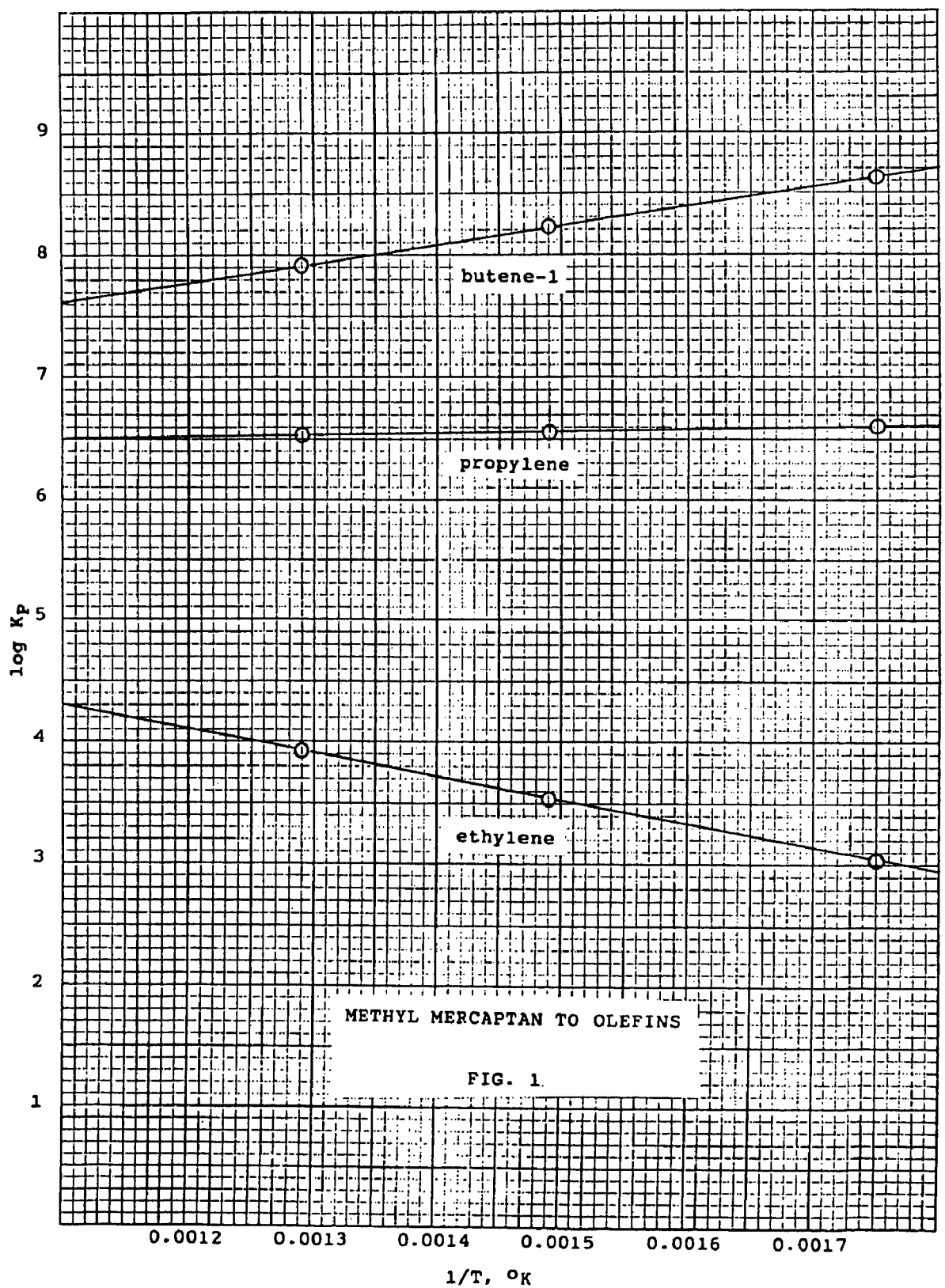
FIG. 1 METHYL MERCAPTAN TO OLEFINS

FORMATION OF OLEFINS FROM METHYL MERCAPTAN

CROSS-REFERENCE TO A RELATED APPLICATION

This application is a continuation of Ser. No. 11/443,885 filed May 31, 2006, currently pending, the contents of which are incorporated herein in its entirety.

FIELD OF THE INVENTION

The present invention relates to a process for manufacturing olefins, including ethylene, propylene and butenes, from methyl mercaptan, also known as methanethiol. In the process, methyl mercaptan undergoes a chemical reaction to produce the olefin and hydrogen sulfide. By recycling the hydrogen sulfide to generate more methyl mercaptan, a stand-alone process is feasible.

BACKGROUND OF THE INVENTION

New technology has been reported for the synthesis of olefins from methanol. (*Chemical Engineering*, January 1996, p. 17). As described in the literature, this process converts methanol in a fluidized-bed reactor at a pressure between 1 and 5 atmospheres and a temperature in the range of 350° C. to 500° C. A zeolite-type catalyst consisting of silicon-aluminum-phosphorus oxide is used to promote the reaction.

The process is capable of converting at best about 80 percent of the methanol to ethylene and propylene in varying proportions of these olefins. Although this process promises to free manufacturers from reliance on traditional feedstocks, e.g., naphtha, it nevertheless is tied to the economics of methanol. These limitations have delayed the large-scale application of this new technology.

Therefore, it is an object of the present invention to offer an improved method for the manufacture of olefins. This object as well as other features and advantages will be apparent from the following description and the FIGURE that is included.

SUMMARY OF THE DISCLOSURE

A process is provided for the synthesis of olefins, including ethylene, propylene and butenes, from methyl mercaptan. A novel chemical reaction is employed whereby two or more methyl mercaptan molecules combine to form the desired olefin plus byproduct hydrogen sulfide. This reaction occurs in pyrolysis when methyl mercaptan is heated to a sufficiently high temperature.

A catalyst is not necessary; however, one may be employed in the reaction to provide improved yields of product or to give greater selectivity of a desired olefin. Such a catalyst may comprise thorium oxide or silicon-aluminum-phosphorous oxide.

Although the reaction may be carried out in a wide range of temperatures, the preferred operating condition is between about 300° C. and about 600° C. Likewise, a wide range of pressures can be used. From a practical standpoint, however, the favored pressure is in the range of about 1 atmosphere to approximately 5 atmospheres.

For maximum efficiency, a continuous reactor is employed. As required, a furnace may be used to provide sufficient heat for the process. The reactor effluent is quenched before recovering the product.

Other applications of the present invention will become apparent to those skilled in the art when the following description of the best mode contemplated for practicing the invention is read in conjunction with the accompanying drawing.

BRIEF DESCRIPTION OF THE DRAWING

The description herein makes reference to the accompanying drawing wherein like reference numerals refer to like parts throughout the drawing, and wherein:

FIG. 1 is a graph showing the equilibrium conversions of methyl mercaptan to ethylene, propylene, and butene-1 at given temperatures.

DETAILED DESCRIPTION OF THE PROCESS

The process of the present invention comprises a chemical reaction wherein methyl mercaptan ($CH_3SH$) is pyrolyzed to form an olefin plus hydrogen sulfide ($H_2S$). The olefin may include ethylene ($C_2H_4$), propylene ($C_3H_6$), and butene ($C_4H_8$). In addition, some higher olefins will inevitably be formed. By adjusting the reaction conditions or employing a specific catalyst, the ratios of these various olefins may be modified. Thus, the process can yield a mixture containing 50 percent ethylene and 30 percent propylene or a mixture with 40 percent ethylene and 40 percent propylene.

The reactions for the formation of ethylene, propylene, and butene can be illustrated by the following equations:

$$2CH_3SH \rightarrow C_2H_4 + 2H_2S \qquad 1.$$

$$3CH_3SH \rightarrow C_3H_6 + 3H_2S \qquad 2.$$

$$4CH_3SH \rightarrow C_4H_8 + 4H_2S \qquad 3.$$

These reactions are carried out in the gas phase.

The conversions of methyl mercaptan to various olefins under equilibrium conditions can be determined by thermodynamic calculations. These results are shown in FIG. 1 for ethylene, propylene, and butene-1, where the logarithm of the equilibrium constant $K_p$ is plotted against the reciprocal of the absolute temperature T. At all the temperatures shown, the equilibrium constants are highly favorable for the reactions. The temperature range shown in FIG. 1 is equivalent to 282° C. to 635° C.

Thermodynamic calculations also indicate that the formation of ethylene is endothermic, whereas the formation of propylene is very slightly exothermic, and the formation of butene-1 is more exothermic. Heat will probably need to be supplied to the reactor to bring the feed up to operating temperature and maintain it at this level.

Methyl mercaptan will decompose by a series of free radical reactions to form the desired olefins. These reactions can be represented by the following equations for the formation of ethylene.

$$CH_3SH \rightarrow CH_3 \cdot + HS \cdot \qquad 4.$$

$$CH_3SH + CH_3 \cdot \rightarrow C_2H_5SH + H \cdot \qquad 5$$

$$CH_3SH + H \cdot \rightarrow CH_3 + H_2S \qquad 6$$

$$C_2H_5SH \rightarrow C_2H_4 + H_2S \qquad 7$$

In the above set of equations, the reaction shown by equation 4 is the initiator and will occur at a sufficiently high temperature. In this reaction, methane mercaptan decomposes by homolysis to produce the two free radicals shown.

Equations 5 and 6 represent chain reactions. They are self-propagating and occur rapidly. The ethanethiol ($C_2H_5SH$) formed in the chain reactions decomposes to ethylene and hydrogen sulfide as indicated by equation 7. Both equations 4 and 7 are well known. (Kirk-Othrmer $4^{th}$ ed., Vol. 24, John Wiley & Sons, p. 27) When equations 5, 6, and 7 are combined, the result is the same as equation 1.

Although a process based on pyrolysis has many advantages, including simplicity and low capital investment, there may be occasion to employ a catalyst. Frequently a catalyst permits operation at lower temperatures, gives improved yields, and provides some control over product selectivity.

An effective catalyst can be determined from the reaction mechanism. Such a mechanism is postulated for the present invention as follows:

$$2CH_3SH + 2H_2O \rightarrow 2CH_3OH + 2H_2S \qquad 8.$$

$$2CH_3OH \rightarrow C_2H_4 + 2H_2O \qquad 9.$$

where $CH_3OH$ is the formula for methanol and $H_2O$ represents water. By adding equations 8 and 9 together, equation 1 is obtained.

Equation 8 is the reverse reaction of the standard preparation for mercaptans from alcohols. (Conant, J. B. and Blatt, A. H., *The Chemistry of Organic Compounds*, $3^{rd}$ ed., the MacMillan Co., New York 1947) The reaction is catalyzed by thorium oxide at a temperature of 350° C. Equation 9 represents the prior art synthesis of olefins from methanol.

Based on the above analysis, a suitable catalyst would comprise thorium oxide and silicon-aluminum-phosphorus oxide. Such a catalyst would be effective at a temperature in the range of 300° C. to 600° C. Pressure is less critical, any low pressure setting being acceptable. Limitations placed on equipment would favor a pressure in the range of 1 to 5 atmospheres.

From equations 8 and 9, it is noted that water is an intermediate in these reactions. Quite likely, there is sufficient moisture present in the feed gas to initiate these reactions. Otherwise, some water may be chemisorbed on the catalyst.

The present invention unavoidably generates the byproduct hydrogen sulfide, which has few applications in industry. Therefore, some means must be found to recycle this material. One solution would be to react hydrogen sulfide with synthesis gas containing carbon monoxide and hydrogen to produce additional methyl mercaptan. In this manner, the process could be made self-supporting.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A process for the manufacture of olefins consisting of pyrolysis of methyl mercaptan by heating methyl mercaptan, in the absence of a catalyst, in a gas phase to a temperature in the range of 300° C. to 600° C., wherein an olefin and hydrogen sulfide are formed by a series of free radical reactions and wherein the recycling of the hydrogen sulfide so formed produces additional methyl mercaptan.

2. The process according to claim 1 in which the olefin is ethylene.

3. The process according to claim 1 in which the olefin is propylene.

4. The process according to claim 1 in which the olefin is butene.

5. The process according to claim 1 in which the pyrolysis is carried out at a pressure in the range of 1 atmosphere to 5 atmospheres.

* * * * *